Figure 1:
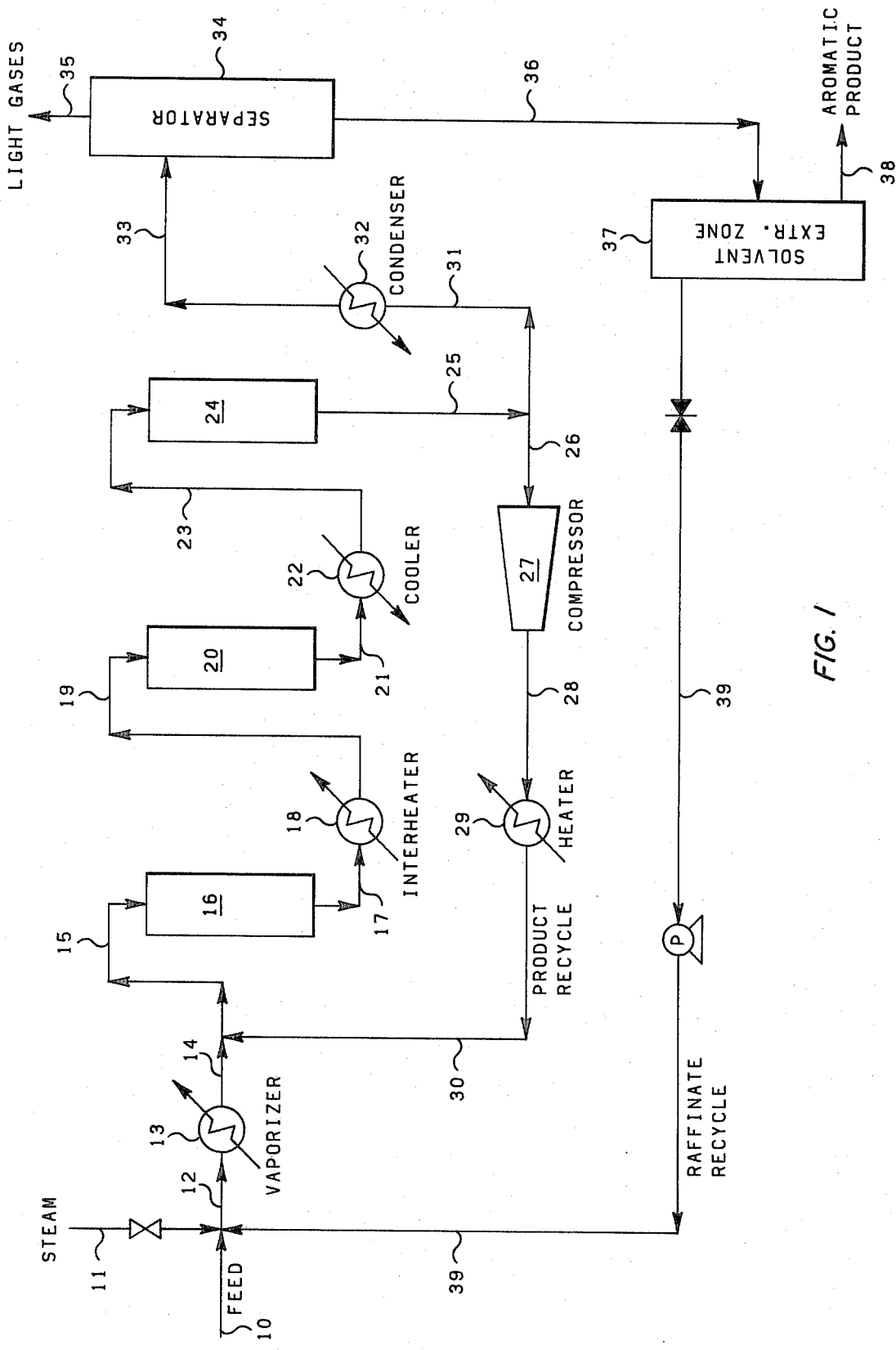

United States Patent [19]

Brinkmeyer et al.

[11] 4,229,602
[45] Oct. 21, 1980

[54] DEHYDROCYCLIZATION PROCESS

[75] Inventors: Francis M. Brinkmeyer; Donald M. Haskell, both of Bartlesville, Okla.

[73] Assignee: Phillips Petroleum Company, Bartlesville, Okla.

[21] Appl. No.: 966,457

[22] Filed: Dec. 4, 1978

[51] Int. Cl.² .................. C07C 5/36; C10G 35/04
[52] U.S. Cl. .............................. 585/407; 208/66; 208/134
[58] Field of Search .................. 208/66, 134; 585/407

[56] References Cited

U.S. PATENT DOCUMENTS

| | | |
|---|---|---|
| 2,439,934 | 4/1948 | Johnson et al. .................. 208/64 |
| 2,891,901 | 6/1959 | Donaldson ........................ 208/64 |
| 2,917,454 | 12/1959 | Dennis .............................. 208/134 |
| 3,401,111 | 9/1968 | Jackson ............................ 208/134 |
| 3,644,196 | 2/1972 | Lawson ............................ 208/62 |
| 3,914,171 | 10/1975 | Schoennagel .................... 208/135 |

Primary Examiner—Herbert Levine

[57] ABSTRACT

A process for catalytic reforming of hydrocarbons which comprises contacting aliphatic hydrocarbons with steam and a dehydrocyclization catalyst under dehydrocyclization conditions to form a vapor stream containing aromatics and nonaromatics, separating at least a portion of the vapor stream which is compressed, heated, and recycled to the dehydrocyclization reaction to minimize steam diluent requirements for the process.

8 Claims, 1 Drawing Figure

DEHYDROCYCLIZATION PROCESS

This invention relates to reforming hydrocarbons. In another aspect, this invention relates to the conversion of aliphatic hydrocarbons to aromatic hydrocarbons in a steam-active dehydrocyclization process wherein steam used at the start of the process is gradually replaced by recycle of a vapor stream separated from the process effluent. In accordance with a further aspect, this invention relates to a steam-active dehydrocyclization process for converting paraffins to aromatics wherein a portion of the reactant effluent vapor, preferably after hydrogenation to remove impurities, is compressed, heated, and recycled to the dehydrocyclization reaction to minimize steam diluent requirements.

The dehydrocyclization reaction for the production of aromatics from normal paraffins is highly endothermic. In one mode of operation, a fixed bed adiabatic reactor using steam as a diluent is used. The steam serves two purposes, namely, (1) lowers the reactant partial pressure and (2) functions as a heat sink to provide the heat of reaction. A minimum mole ratio of steam to hydrocarbon feed of 5:1 is believed necessary, and studies have shown improved product quality and quantity with increased steam as high as 15:1. The use of steam as a diluent requires considerable energy to generate the steam required. In accordance with the invention, a hydrocarbon diluent vapor stream instead of steam is used as the reaction diluent after startup, and considerable savings of energy costs are realized. The diluent vapor stream recycle contains nonaromatics which can be converted to aromatics in the recycling thereof. The recycle stream is not condensed prior to recycle thereof to the reforming zone.

Accordingly, an object of this invention is to provide an improved process for dehydrocyclization of nonaromatic hydrocarbons.

Another object of this invention is to reduce energy costs in a reforming process.

A further object of this invention is to provide a diluent stream other than steam in a reforming process.

Other objects and aspects, as well as the several advantages of the invention, will be apparent to those skilled in the art upon reading the specification, the drawing, and the appended claims.

In accordance with the invention, aliphatic hydrocarbons, especially paraffins, are contacted with steam and a dehydrocyclization catalyst under dehydrocyclization conditions to produce a vapor stream comprising aromatics and nonaromatic hydrocarbons, and at least a portion of the vapor stream is compressed to increase the pressure, heated to approximately the dehydrocyclization temperature, and recycled to the dehydrocyclization reaction to minimize steam diluent requirement.

The amount of vapor product recycled to the dehydrocyclization reaction is gradually increased after startup of the process until all or essentially all of the steam has been replaced. In other words, as the process gets under way, the amount of recycle can be increased and the amount of steam added to the process decreased in order to maintain dehydrocyclization conditions. The invention, using hydrocarbon diluent instead of steam after startup, will save about 35 percent in energy costs. This occurs because the hydrocarbon diluent recycle stream contains nonaromatics which become aromatics in the recycling thereof, the recycled vapor stream is not condensed and revaporized prior to introduction into the dehydrocyclization reactor, and steam costs are reduced. The aromatics in the recycle hydrocarbon stream also serve as part of the diluent.

The invention is particularly applicable to the dehydrocyclization and reforming of hydrocarbons including acyclic and cyclic paraffins, particularly naphthenes and paraffins. The invention is particularly suitable for the reformation of paraffins containing six or more carbon atoms per molecule including n-hexane, methylhexane, n-heptane, dodecane, and the like. Some examples of naphthenes which can be reformed are methylcyclopentane, cyclohexane, and the like. Some olefins can be present in the feedstock. The preferred feeds range from $C_6$ to $C_{12}$ paraffins. Mixtures of paraffins and naphthenes such as are obtained from the distillation of straight run or natural gasolines can be used. Most often, refinery streams containing such materials and boiling in the range of from about 150°–400° F. are used. Low sulfur-containing feeds are generally preferred.

The foregoing hydrocarbons to be subjected to dehydrocyclization and reforming are contacted with a suitable dehydrocyclization catalyst at a temperature and flow rate of hydrocarbon feedstock in the presence of steam or recycled hydrocarbon diluent sufficient to convert the hydrocarbon feedstock to the desired reformed aromatic product. The conditions employed will vary appreciably, depending upon the hydrocarbon feedstock used. Generally, the temperature employed will be in the range of 600°–1200° F., preferably 900°–1150° F., and more preferably about 1070° to about 1120° F. The pressure in the reforming reaction for the purposes of the present invention is generally in the range of 60–120 psig. The hydrocarbon feed rate for use in the present invention, i.e., the weight hourly space velocity (WHSV), is in the range of 1–4. The molar ratio of steam to fresh feed initially is in the range of 5:1 to 25:1, and, as the reaction progresses, the steam is replaced with a recycle vapor hydrocarbon diluent stream. The final mole ratio of steam to fresh feed can be minimal, even zero. The recycle vapor hydrocarbon used to replace steam can be in the mole ratio range of about 3:1 to about 8.5:1 of the fresh feed.

Catalysts that can be used in the dehydrocyclization reaction are generally of the platinum type in combination with suitable supports, as well as other promoter metals. Representative catalysts include platinum-alumina, platinum-silica, platinum-tin-zinc aluminate, and the like.

In accordance with one specific embodiment of the invention, the vapor effluent from the dehydrocyclization reaction is subjected to hydrogenation to remove impurities present, such as diolefins. The aromatic-containing reformate can be subjected to hydrogenation conditions including a temperature in the range of about 500°–700° F., a pressure of 60–120 psig, a weight hourly space velocity (WHSV) of fresh feed to catalyst of 3–10, and a suitable hydrogenation catalyst such as Group VIII metals, for example, platinum or palladium on alumina, nickel-alumina, and the like.

A better understanding of the invention will be obtained upon reference to the drawing illustrating a preferred embodiment of the invention.

Referring now to the drawing, a hydrocarbon feed such as a normal paraffin feed of hydrocarbons having at least six carbon atoms per molecule is introduced into the system by way of line 10 and mixed with steam introduced by way of valved line 11, and the mixture passed by way of line 12 through heater 13 where the feed mixture, including steam, is heated to reforming reaction conditions. The heated feed is removed from heater 13 by way of line 14 and passed by line 15 to dehydrocyclization reactor 16. In this embodiment of the invention, there are two dehydrocyclization reactors and one hydrogenation reactor arranged in series, but more reactors can be used if desired.

The hydrocarbon feed and steam or recycle diluent are passed at a temperature of about 900°–1100° F. through reactor 16 containing a fixed bed of dehydrocyclization catalyst such as platinum-tin-zinc aluminate wherein the hydrocarbon feed is subjected to dehydrocyclization conditions and at least a portion of the feed is converted to aromatics. The effluent removed from reactor 16 is passed by line 17 through heater 18 and introduced by line 19 into the second dehydrocyclization reactor 20. Dehydrocyclization reactor 20 is operated under substantially the same condition and can contain the same catalyst as reactor 16.

Reactor 20 effluent comprising aromatic product, e.g., benzene, toluene, and the like, and nonaromatic hydrocarbons such as paraffinic feed, e.g., heptane, as well as lighter paraffins and aromatics, is removed by line 21, cooled by heat exchanger 22, and passed by line 23 to hydrogenation reactor 24. The hydrogenation reactor operates at a lower temperature than the dehydrocyclization reactors, and therefore the reformate feed needs to be cooled prior to introduction into reactor 24.

The reformate introduced into hydrogenation reactor 24 contains hydrogen and when the feed together with hydrogen contacts a suitable hydrogenation catalyst in reactor 24, e.g., tin-platinum on zinc aluminate, the unsaturated impurities, such as diolefins, present will be hydrogenated and converted to saturated and olefinic materials. The hydrogenated vaporous reformate is removed from reactor 24 by line 25.

In accordance with the invention, the vaporous effluent in line 25 is divided and at least a portion is removed by line 26 and passed through a compressor or other suitable means for elevating the pressure of the vapor stream. In this embodiment, compressor 27 increases the pressure of the vapor stream to a pressure of about 95 to 100 psig, and after compression the stream is passed by line 28 to heater 29 where the temperature is increased to about 950° F. or higher. The heated reformate vapor is passed by line 30 as recycle and introduced into line 14, the reforming zone feed line. As the amount of recycle is increased during the process, the amount of steam introduced by line 11 is reduced until essentially all, if not all, of the steam is replaced with recycle reformate vapor.

The remainder of the reformate not recycled to zone 16 is passed by way of line 31 to heat exchanger 32 wherein it is cooled and partially condensed and the condensate is passed by way of line 33 to a suitable separation zone, e.g., distillation zone 34. Light gases are taken overhead by line 35 and removed from the system. Separation zone 34 can be operated at a pressure range of 25–50 psig and a temperature in the range of 70°–105° F.

Condensate or reformed liquid product removed from separator 34 by way of line 36 is passed to solvent extraction zone 37 wherein it is contacted with a suitable solvent such as sulfolane, phenol, liquid $SO_2$, methyl pyrrolidone, tetramethyleneglycol, dimethylsulfoxide, dimethylformamide, diethyleneglycol, and the like. Suitable conditions for zone 37 include a pressure in the range of 5–40 psig and a temperature in the range of 120°–250° F. Zone 37 can be two liquid phase extractive distillation.

Aromatic product, for example, benzene, toluene, and the like, is removed from zone 37 by way of line 38, and a paraffinic fraction (raffinate) is removed by way of line 39 and recycled to zone 16 as part of the feed and is introduced into feed line 12 for conversion to additional aromatic product.

EXAMPLE

The following is a calculated example based upon a process flow, as illustrated in the drawing, having two dehydrocyclization reactors with a fixed bed of catalyst in each and a single fixed bed hydrogenation reactor followed by suitable heat exchange and separation equipment. The numbering of the flow lines and equipment corresponds to the drawing. The conditions obtaining in the different units of the process are as follow:

|  | Best Mode |
|---|---|
| Reactors 16 and 20: | |
| Pressure, psig | 90 |
| Inlet temperature, °F. | 1095 |
| Wt. hourly space velocity of fresh feed to catalyst, lb/lb | 1.5 |
| Steam/fresh feed mole ratio[a] | |
| Initial | 8:1 |
| Final | 0 |
| Recycle 30 from reactor 24/fresh feed mole ratio[a] | |
| Initial | 0 |
| Final | 6.4:1 |
| Conversion of fresh feed to aromatics, wt. % | 69 |
| Reactor 24: | |
| Pressure, psig | 90 |
| Inlet Temperature, °F. | 650 |
| Weight hourly space velocity of fresh feed to catalyst, lb/lb | 3 |
| Carbonyls, diolefins, acetylenes, etc., in effluent | Nil |

[a]At startup there is insufficient Reactor 24 effluent for recycle. During operation, the recycle 30 from Reactor 24 gradually replaces the diluent steam, ultimately shutting off steam, preferably entirely using this recycle as the diluent. The mole ratio of the moles of steam 11 plus moles of recycle 30 to the fresh feed is at least about 3:1 during this changeover from steam to recycle.
Catalyst in Reactors 16 and 20 is 0.6 weight percent platinum, 1.0 weight percent tin on $ZnAl_2O_4$.

Catalyst used (specifically for Best Mode) is platinum and tin or zinc aluminate (0.6 weight percent platinum, 1 weight percent tin).

| Separator 34: | |
|---|---|
| Pressure, psig | 35 |
| Temperature, °F. | 90 |
| Solvent Extraction 37[b]: | |
| Pressure, psig | 25 |
| Temperature, °F. | 200 |

[b]Optional to solvent extract to concentrate aromatics recovered in the extract phase and recycle nonaromatic raffinate 39 back to Reactor 16. Sulfolane and water usually used as solvent.

| | Calculated Flow and Compositions | | |
|---|---|---|---|
| (10) | Feed Hydrocarbon, bbl/day | | 10,000 |
| | Composition | wt. % | |
| | Normal heptane | 97.0 | |
| | Lighter paraffins | 1.5 | |
| | Heavier paraffins | 1.5 | |
| (39) | Recycle Nonaromatics, bbl/day[c] | | 5,870 |

-continued

Calculated Flow and Compositions

| | | | |
|---|---|---|---|
| (11) | Steam, 1500° F., 130 psig | | |
| | Initial, pounds/day | | 5,164,000 |
| | Final | | 0 |
| (30) | Final Quantity Recycle Vapor from Reactor 24 (at 0 steam), SCF/day[d] | | 57.9 × 10[6] |
| | Compositon | wt. % | |
| | Hydrogen | 5.9 | |
| | Toluene | 42.1 | |
| | Normal heptane | 35.9 | |
| | Lighter paraffins | 12.9 | |
| | Heavier paraffins | 0.9 | |
| | Lighter aromatics | 2.3 | |
| (36) | Separator 34 Yield, bbl/day[e] | | 11,413 |
| | Composition | wt. % | |
| | Hydrogen | — | |
| | Toluene | 51.5 | |
| | Normal heptane | 43.9 | |
| | Lighter paraffins | 0.7 | |
| | Heavier paraffins | 1.1 | |
| | Lighter aromatics | 2.8 | |

[c]Recycle is used in illustrative example.
[d]When steam addition is zero.
[e]H$_2$ of SCF/day not included, 46.8 × 10$^6$.

The use of recycle hydrocarbon 30 diluent for steam, after startup, can save about 35 percent of the energy costs for the operation as compared with using only steam 11 as diluent. A mixture of diluent steam and recycle hydrocarbon can, of course, be used. It is now preferred to use finally only recycle 30, however.

We claim:

1. A process for producing aromatics from aliphatic hydrocarbons which comprises the steps of
   (a) contacting a feed comprising aliphatic hydrocarbons with steam and a dehydrocyclization catalyst under steam-active dehydrocyclization conditions sufficient to form a vapor stream comprising aromatics, nonaromatics, and hydrogen,
   (b) separating at least a portion of said vapor stream and increasing the pressure thereof by compressing same and then heating the compressed vapor to approximately the dehydrocyclization temperature and pressure, and
   (c) recycling said compressed and heated vapor stream to the dehydrocyclization reaction in step (a) at a gradually increased rate such that the amount of steam diluent used in (a) is gradually reduced after startup of the process to a point where the steam is replaced or substantially replaced with said recycle as the diluent for the process.

2. A process according to claim 1 wherein the dehydrocyclization vapor effluent is first subjected to hydrogenation in the presence of a hydrogenation catalyst under hydrogenation conditions sufficient to remove unsaturated impurities prior to compressing, heating, and recycling said portion to said dehydrocyclization reaction in step (a).

3. A process according to claim 1 wherein the remainder of said vapor not separated and recycled is cooled sufficiently to condense said vapor stream and form a liquid product stream and separating said liquid product stream into an aromatic product and an aliphatic stream which is recycled to step (a).

4. A process according to claim 1 wherein the dehydrocyclization vapor effluent is first subjected to hydrogenation in the presence of a hydrogenation catalyst under hydrogenation conditions sufficient to remove unsaturated impurities, and wherein the remainder of said vapor stream not separated and recycled is cooled sufficiently to condense said vapor stream and form a liquid product stream, and separating said liquid product into an aromatic product and an aliphatic stream which is recycled to step (a).

5. A process according to claim 4 wherein step (a) comprises a plurality of fixed beds of dehydrocyclization catalyst and at least one fixed bed of hydrogenation catalyst.

6. A process according to claim 1 wherein the initial amount of steam in the process ranges from 5:1 to 25:1 based on a mole ratio of steam to fresh feed and the final amount can be decreased to a minimal amount during the process, and the initial amount of vapor recycle is zero at startup and is increased as the process progresses until the amount ranges from 3:1 to 8.5:1 based on a mole ratio of recycle to fresh feed.

7. A process according to claim 1 wherein said feed to (a) comprises heptane which is converted to toluene and the recycle vapor stream (c) comprises hydrogen, toluene, heptane, and other lighter paraffins and aromatics.

8. A process according to claim 3 wherein the remainder of said vapor stream not separated and recycled is fractionated to separate overhead light gases therefrom and the liquid fraction is subjected to solvent extraction to separately recover an aromatics product stream and an aliphatic hydrocarbon stream which is recycled to (a).

* * * * *